United States Patent
Badran et al.

(10) Patent No.: US 11,771,893 B2
(45) Date of Patent: Oct. 3, 2023

(54) MOTION-ACTIVATED, CLOSED-LOOP NON-INVASIVE VAGUS NERVE STIMULATION FOR NEUROREHABTLITATION

(71) Applicant: MUSC Foundation for Research Development, Charleston, SC (US)

(72) Inventors: Bashar Badran, Charleston, SC (US); Mark S. George, Sullivans Island, SC (US)

(73) Assignee: MUSC Foundation for Research Development, Charleston, SC (US)

( * ) Notice: Subject to any disclaimer, the term of this patent is extended or adjusted under 35 U.S.C. 154(b) by 0 days.

(21) Appl. No.: 17/619,950

(22) PCT Filed: Jun. 29, 2020

(86) PCT No.: PCT/US2020/040121
§ 371 (c)(1),
(2) Date: Dec. 16, 2021

(87) PCT Pub. No.: WO2020/264496
PCT Pub. Date: Dec. 30, 2020

(65) Prior Publication Data
US 2022/0296889 A1   Sep. 22, 2022

Related U.S. Application Data

(60) Provisional application No. 62/867,989, filed on Jun. 28, 2019.

(51) Int. Cl.
*A61N 1/32* (2006.01)
*A61N 1/36* (2006.01)
*A61N 1/04* (2006.01)

(52) U.S. Cl.
CPC .......... *A61N 1/326* (2013.01); *A61N 1/0456* (2013.01); *A61N 1/36031* (2017.08); *A61N 1/36034* (2017.08)

(58) Field of Classification Search
CPC .. A61N 1/326; A61N 1/0456; A61N 1/36031; A61N 1/36034
See application file for complete search history.

(56) References Cited

U.S. PATENT DOCUMENTS

| 5,514,175 A | 5/1996 | Kim |
| 9,089,691 B2 | 7/2015 | Libbus |

(Continued)

FOREIGN PATENT DOCUMENTS

| IL | WO 2018/109633 A1 * | 6/2018 | ............... A61N 1/36 |
| WO | 2014136852 A1 | 9/2014 | |
| WO | 2018109633 A1 | 6/2018 | |

OTHER PUBLICATIONS

International Search Report and Written Opinion issued in PCT/US2020/040121, dated Sep. 30, 2020, 11 pages.

*Primary Examiner* — Amanda K Hulbert
*Assistant Examiner* — Philip C Edwards
(74) *Attorney, Agent, or Firm* — Riverside Law LLP

(57) ABSTRACT

A system for neurorehabilitation is disclosed that includes a motion detector configured to generate a motion detection feedback signal, a transcutaneous auricular vagus nerve stimulation module, and a controller configured to receive the motion detection feedback signal and send a stimulation signal to the transcutaneous auricular vagus nerve stimulation module based on the motion detection feedback signal meeting a minimum threshold criteria. A method for neurorehabilitation is disclosed that includes the steps of detecting patient motor activity, determining if the detected patient motor activity meets a minimum threshold criteria, and (Continued)

stimulating a vagus nerve through transcutaneous auricular vagus nerve stimulation if the minimum threshold criteria is met.

7 Claims, 4 Drawing Sheets

(56) References Cited

U.S. PATENT DOCUMENTS

| | | |
|---|---|---|
| 9,533,152 B2 | 1/2017 | Kilgard |
| 10,252,074 B2 | 4/2019 | Simon |
| 2008/0234781 A1 | 9/2008 | Einav |
| 2012/0083700 A1 | 4/2012 | Osorio |
| 2013/0310909 A1* | 11/2013 | Simon ................ A61N 1/36025 |
| | | 607/115 |
| 2013/0317580 A1 | 11/2013 | Simon |
| 2015/0018667 A1* | 1/2015 | Radman ................ A61B 5/389 |
| | | 607/45 |
| 2015/0073493 A1* | 3/2015 | Kilgard ................ G09B 23/28 |
| | | 607/3 |
| 2016/0339238 A1 | 11/2016 | Ahmed |
| 2019/0355476 A1* | 11/2019 | Li ........................... G06F 17/11 |

* cited by examiner

MOTION-ACTIVATED, CLOSED-LOOP NON-INVASIVE VAGUS NERVE STIMULATION FOR NEUROREHABTLITATION

CROSS-REFERENCE TO RELATED APPLICATIONS

This application is a U.S. national stage filing of international application no. PCT/US20/40121 filed on Jun. 29, 2020, which claims priority to U.S. provisional application No. 62/867,989, filed Jun. 28, 2019, both of which are incorporated herein by reference in their entireties.

STATEMENT REGARDING FEDERALLY SPONSORED RESEARCH OR DEVELOPMENT

This invention was made with government support under grant number 5P20 GM109040-04 awarded by the National Institutes of Health. The government has certain rights in the invention.

BACKGROUND OF THE INVENTION

Nearly 800,000 people in the United States have a stroke annually, with motor impairments being the most common long-term functional disability. 85% of stroke cases result in reductions in upper limb function, and this has a severe negative impact on daily living. Motor recovery is achieved most commonly through professionally assisted motor rehabilitation training, and experimentally through various robotic, virtual reality, and brain stimulation techniques. Many of these rehabilitation techniques attempt to restore pathologically insufficient neural activity post-stroke to regain function, as the stroke induces damage to brain tissue and subsequent reorganization of cortical motor representations in surrounding undamaged tissue.

Invasive cervical vagus nerve stimulation (invasive cVNS) is a surgically invasive neuromodulation technique developed in the 1980's to treat intractable epilepsy and chronic refractory major depression. Invasive cVNS involves wrapping a cuff electrode around the left cervical bundle of the vagus nerve and has seen a reemergence in the past decade following several promising animal model findings demonstrating the ability to induce neuroplasticity in a target-dependent manner. In animal models, the temporal pairing of cVNS bursts paired with motor rehabilitation can restore pathologically insufficient neural activity post-stroke or correct maladaptive activity in tinnitus. This intricate pairing of VNS and restorative behavioral intervention is known as "targeted plasticity" and is a promising approach to treatment of neuropsychiatric interventions, with potentially transformative potential in post stroke rehabilitation.

Underlying basic fundamentals of neuroplasticity is the release of neuromodulators that influence this dynamic neural process. Plasticity may be endogenously influenced (via repeated behavioral training) or exogenously influenced (via noninvasive brain stimulation). One of these exogenous influencers of plasticity is vagus nerve stimulation (VNS), which delivers electricity to the vagus nerve, sending an afferent signal to the brainstem, activating the brain's primary source of norepinephrine (locus coeruleus) which results in broad downstream neuroplastic cellular effects. Lesions to locus coeruleus inhibit this noradrenergic-driven neuroplasticity. VNS is an influencer of neural plasticity and has been paired with various forms of training in animal models to restore deficient or aberrant neural activity. Most notably, rats with implanted VNS electrodes were concurrently stimulated while receiving rehabilitative training post-ischemic stroke induction. In one study, 100% of the rats receiving the paired intervention fully recovered forelimb function compared to 22% of rats in the control condition. Cortical reorganization in the VNS group restored pathologically inactive circuits. These findings have led to large scale clinical trials (Microtransponder, 2012) exploring the use of VNS-paired rehabilitation to restore upper limb function and are early positive indications of using paired-therapy for rehabilitation.

Recently, a noninvasive alternative known as transcutaneous auricular vagus nerve stimulation (taVNS) has emerged as a promising alternative to conventionally implanted cVNS. taVNS, however, targets the auricular branch of the vagus nerve, which innervates the human ear and activates the afferent and efferent vagal networks, allowing for a noninvasive, simple, and rapid translation of cervically implanted VNS findings. Although paired taVNS rehab is promising, there is no reliable system or method for translating this rehab modality into the clinic.

Thus, there is a need in the art for an improved noninvasive form of stroke rehabilitation that shortens treatment time, does not permanently rely on the use medical devices, and does not rely on expensive equipment or prolonged treatment, therefore providing superior patient outcomes and accelerated recovery times, all at a lower cost to patients and healthcare providers.

SUMMARY OF THE INVENTION

In one embodiment, a system for neurorehabilitation includes a motion detector configured to generate a motion detection feedback signal, a transcutaneous auricular vagus nerve stimulation module, and a controller configured to receive the motion detection feedback signal and send a stimulation signal to the transcutaneous auricular vagus nerve stimulation module based on the motion detection feedback signal meeting a minimum threshold criteria. In one embodiment, the transcutaneous auricular vagus nerve stimulation module comprises a surface electrode. In one embodiment, the controller is configured to synchronize delivery of the stimulation signal with a detected motion with a delay of 2 seconds or less. In one embodiment, the controller is configured to synchronize delivery of the stimulation signal with a detected motion with a delay of 1 second or less. In one embodiment, the controller is configured to synchronize delivery of the stimulation signal with a detected motion with a delay of 100 ms or less. In other embodiments, the controller is configured to synchronize delivery of the stimulation signal with the detected motions with a delay of 900 ms, 800 ms, 700 ms, 600 ms, 500 ms, 400 ms, 300 ms, or 200 ms. In other embodiments, the controller is configured to synchronize delivery of the stimulation signal with the detected motions with a delay of 90 ms, 80 ms, 70 ms, 60 ms, 50 ms, 40 ms, 30 ms, 20 ms or 10 ms. In one embodiment, the stimulation signal comprises an electrical intensity greater than 0 mA and up to 10 mA, a frequency of greater than 0 Hz and up to 100 Hz, and a pulse width greater than 0ps and up to 1000 μs. In one embodiment, the stimulation signal comprises an electrical intensity greater than 0.5 mA and up to 5 mA, a frequency of greater than 10 Hz and up to 50 Hz, and a pulse width greater than 100 μs and up to 500 μs. In one embodiment, the stimulation signal comprises an electrical intensity greater than 1 mA and up to 3 mA, a frequency of greater than 25 Hz and up to 50 Hz, and a pulse width greater than 250 µs and up to 500 µs.

In one embodiment, the stimulation is a theta burst stimulation, wherein stimulation is applied in a triplicate pattern in that stimulation is grouped into sets of three burst applied in rapid succession, with: an intensity greater than 0 mA and up to 10 mA, more specifically greater than 0.5 mA and up to 5 mA, and most specifically greater than 1 mA and up to 5 mA; wherein each burst within a triplet possesses a frequency greater than 0 Hz and up to 100 Hz, more specifically greater than 25 Hz and up to 75 Hz, and most specifically greater than 40 Hz and up to 60 Hz, and wherein the group of triplets possess a frequency of greater than 0 Hz and up to 100 Hz, more specifically greater than 1 Hz and up to 25 Hz, and most specifically greater than 1 Hz and up to 10 Hz; and a pulse width greater than 0ps and up to 1000 µs, more specifically greater than 100 µs and up to 500 µs, and most specifically greater than 250 µs and up to 500 µs.

In other embodiments the electrical intensity can be: 0.1 mA, 0.2 mA, 0.3 mA, 0.4 mA, 0.5 mA, 0.6 mA, 0.7 mA, 0.8 mA, 0.9 mA, 1.0 mA, 1.1 mA, 1.2 mA, 1.3 mA, 1.4 mA, 1.5 mA, 1.6 mA, 1.7 mA, 1.8 mA, 1.9 mA, 2.0 mA, 2.1 mA, 2.2 mA, 2.3 mA, 2.4 mA, 2.5 mA, 2.6 mA, 2.7 mA, 2.8 mA, 2.9 mA, 3.0 mA, 3.1 mA, 3.2 mA, 3.3 mA, 3.4 mA, 3.5 mA, 3.6 mA, 3.7 mA, 3.8 mA, 3.9 mA, 4.0 mA, 4.1 mA, 4.2 mA, 4.3 mA, 4.4 mA, 4.5 mA, 4.6 mA, 4.7 mA, 4.8 mA, 4.9 mA, 5.0 mA, 5.1 mA, 5.2 mA, 5.3 mA, 5.4 mA, 5.5 mA, 5.6 mA, 5.7 mA, 5.8 mA, 5.9 mA, 6.1 mA, 6.2 mA, 6.3 mA, 6.4 mA, 6.5 mA, 6.6 mA, 6.7 mA, 6.8 mA, 6.9 mA, 7.0 mA, 8.1 mA, 8.2 mA, 8.3 mA, 8.4 mA, 8.5 mA, 8.6 mA, 8.7 mA, 8.8 mA, 8.9 mA, 9.0 mA, 9.1 mA, 9.2 mA, 9.3 mA, 9.4 mA, 9.5 mA, 9.6 mA, 9.7 mA, 9.8 mA, 9.9 mA, or 10 mA.

In other embodiments the frequency can be: 1 Hz, 2 Hz, 3 Hz, 4 Hz, 5 Hz, 6 Hz, 7 Hz, 8 Hz, 9 Hz, 10 Hz, 11 Hz, 12 Hz, 13 Hz, 14 Hz, 15 Hz, 16 Hz, 17 Hz, 18 Hz, 19 Hz, 20 Hz, 21 Hz, 22 Hz, 23 Hz, 24 Hz, 25 Hz, 26 Hz, 27 Hz, 28 Hz, 29 Hz, 30 Hz, 31 Hz, 32 Hz, 33 Hz, 34 Hz, 35 Hz, 36 Hz, 37 Hz, 38 Hz, 39 Hz, 40 Hz, 41 Hz, 42 Hz, 43 Hz, 44 Hz, 45 Hz, 46 Hz, 47 Hz, 48 Hz, 49 Hz, 50 Hz, 51 Hz, 52 Hz, 53 Hz, 54 Hz, 55 Hz, 56 Hz, 57 Hz, 58 Hz, 59 Hz, 61 Hz, 62 Hz, 63 Hz, 64 Hz, 65 Hz, 66 Hz, 67 Hz, 68 Hz, 69 Hz, 70 Hz, 71 Hz, 72 Hz, 73 Hz, 74 Hz, 75 Hz, 76 Hz, 77 Hz, 78 Hz, 79 Hz, 80 Hz, 81 Hz, 82 Hz, 83 Hz, 84 Hz, 85 Hz, 86 Hz, 87 Hz, 88 Hz, 89 Hz, 90 Hz, 91 Hz, 92 Hz, 93 Hz, 94 Hz, 95 Hz, 96 Hz, 97 Hz, 98 Hz, 99 Hz, or 100 Hz In other embodiments the pulse width can be: 10 µs, 20 µs, 30 µs, 40 µs, 50 µs, 60 µs, 70 µs, 80 µs, 90 µs, 100 µs, 110 µs, 120 µs, 130 µs, 140 µs, 150 µs, 160 µs, 170 µs, 180 µs, 190 µs, 200 µs, 210 µs, 220 µs, 230 µs, 240 µs, 250 µs, 260 µs, 270 µs, 280 µs, 290 µs, 300 µs, 310 µs, 320 µs, 330 µs, 340 µs, 350 µs, 360 µs, 370 µs, 380 µs, 390 µs, 400 µs, 410 µs, 420 µs, 430 µs, 440 µs, 450 µs, 460 µs, 470 µs, 480 µs, 490 µs, 500 µs, 510 µs, 520 µs, 530 µs, 540 µs, 550 µs, 560 µs, 570 µs, 580 µs, 590 µs, 610 µs, 620 µs, 630 µs, 640 µs, 650 µs, 660 µs, 670 µs, 680 µs, 690 µs, 700 µs, 710 µs, 720 µs, 730 µs, 740 µs, 750 µs, 760 µs, 770 µs, 780 µs, 790 µs, 800 µs, 810 µs, 820 µs, 830 µs, 840 µs, 850 µs, 860 µs, 870 µs, 880 µs, 890 µs, 900 µs, 910 µs, 920 µs, 930 µs, 940 µs, 950 µs, 960 µs, 970 µs, 980 µs, 990 µs, or 1000 µs.

In one embodiment, the transcutaneous auricular vagus nerve stimulation module comprises a surface electrode configured to interface with an anterior wall of an outer ear canal. In one embodiment, the transcutaneous auricular vagus nerve stimulation module is configured to stimulate an auricular branch of the vagus nerve. In one embodiment, the motion detector comprises one or more of an EMG electrode, an EEG electrode, a camera, a robotic apparatus, an exoskeleton apparatus and an accelerometer. In one embodiment, the muscle activity feedback signals are based on at least one muscle from the group consisting of flexor carpi radialis, flexor capri ulnaris, biceps, triceps, anterior deltoid, middle deltoid, gluteus maximus, quadriceps femoris, anterior compartment of the leg, quadriceps femoris, foot inverters and evertors, biceps femoris, semitendinosus and/or semimembranosus. In one embodiment, the motion detection feedback signal is based on a plurality of muscle activity feedback signals. In one embodiment, the muscle activity feedback signals are based on two or more muscles from the group consisting of flexor carpi radialis, flexor capri ulnaris, biceps, triceps, anterior deltoid and middle deltoid. In one embodiment, the muscle activity signals are based on at least a first signal from an upper limb indicative of movement from one or more of a trapezius, deltoid, biceps brachii, triceps, flexor/extensor carpi radialis, flexor/extensor digitorum, and flexor/extensor pollicis *brevis*; and at least a second signal from a lower limb indicative of movement from one or more of a gluteus maximus, quadriceps femoris, anterior compartment of the leg, quadriceps femoris, foot inverters and evertors, biceps femoris, semitendinosus and semimembranosus. In one embodiment, the minimum threshold criteria comprises an EMG motor evoked potential of at least 50 uV. In one embodiment, the minimum threshold criteria comprises a motion sufficient to be detectable by an accelerometer. In one embodiment, the minimum threshold criteria comprises a motion sufficient to be detectable via a depth camera, video camera or other visual motion sensor device. In one embodiment, the minimum threshold criteria comprises a force sufficient to trigger a pressure sensing floor mat. In one embodiment, the minimum threshold criteria is determined by an observer and manually triggered. In one embodiment, the minimum threshold criteria is a minimum threshold for contraction.

In one embodiment, a method for neurorehabilitation includes the steps of detecting patient motor activity, determining if the detected patient motor activity meets a minimum threshold criteria, and stimulating a vagus nerve through transcutaneous auricular vagus nerve stimulation if the minimum threshold criteria is met. In one embodiment, detecting patient motor activity comprises detecting muscle electrical activity. In one embodiment, detecting patient motor activity comprises detecting a plurality of muscle activity feedback signals. In one embodiment, detecting patient motor activity includes patient imaging. In one embodiment, detecting patient motor activity includes utilizing an accelerometer affixed to the patient. In one embodiment, the minimum threshold criteria comprises a force sufficient to trigger a pressure sensing floor mat. In one embodiment, the minimum threshold criteria is determined by an observer and manually triggered. In one embodiment, the muscle activity feedback signals are based on at least one muscle from the group consisting of flexor carpi radialis, flexor capri ulnaris, biceps, triceps, anterior deltoid, middle deltoid, gluteus maximus, quadriceps femoris, anterior compartment of the leg, quadriceps femoris, foot inverters and evertors, biceps femoris, semitendinosus and/or semimembranosus. In one embodiment, the plurality of muscle activity feedback signals are based on two or more muscles from the group consisting of flexor carpi radialis, flexor capri ulnaris, biceps, triceps, anterior deltoid and middle deltoid. In one embodiment, the plurality of muscle activity feedback signals are based on: at least a first signal from an upper limb indicative of movement from one or more of a trapezius, deltoid, biceps brachii, triceps, flexor/extensor carpi radialis, flexor/extensor digitorum, and flexor/extensor pollicis *brevis*; and at least a second signal from a lower limb indicative of movement from one or more of a gluteus maximus, quadriceps femoris, anterior compartment of the leg, quadriceps femoris, foot inverters and evertors, biceps femoris, semitendinosus and semimembranosus. In one embodiment, detecting patient motor activity comprises mechanical feedback from a robotic or exoskeleton apparatus. In one embodiment, stimulating a vagus nerve comprises stimulating an auricular branch of the vagus nerve. In one embodiment, the minimum threshold criteria comprises one or more of a minimum signal amplitude, a minimum signal frequency, a minimum signal duration, a comparison to a model signal, a comparison to a preset value, and a comparison to a previously measured signal. In one embodiment, delivery of the stimulation is synchronized with a detected motion with a delay of 100 ms or less. In one embodiment, the stimulation comprises an electrical intensity greater than 0 mA and up to 10 mA, a frequency of greater than 0 Hz and up to 100 Hz, and a pulse width greater than 0ps and up to 500 μs. In one embodiment, the stimulation comprises an electrical intensity greater than 0.5 mA and up to 5 mA, a frequency of greater than 10 Hz and up to 25 Hz, and a pulse width greater than 100 μs and up to 250 μs. In one embodiment, the stimulation is delivered to an anterior wall of an outer ear canal. In one embodiment, the minimum threshold criteria comprises an EMG motor evoked potential of at least 50 uV. In another embodiment, the minimum threshold criteria comprises a motion sufficient to be detectable by an accelerometer. In yet another embodiment, the minimum threshold criteria comprises a motion sufficient to be detectable via a depth camera, video camera or other visual motion sensor device. In one embodiment, the minimum threshold criteria comprises a force sufficient to trigger a pressure sensing floor mat. In one embodiment, the minimum threshold criteria is determined by an observer and manually triggered. In one embodiment, the minimum threshold criteria is a minimum threshold for contraction. Notably, any of the embodiment described herein can possess any of the stimulation delays, intensities, frequencies or pulse widths described herein.

BRIEF DESCRIPTION OF THE DRAWINGS

The foregoing purposes and features, as well as other purposes and features, will become apparent with reference to the description and accompanying figures below, which are included to provide an understanding of the invention and constitute a part of the specification, in which like numerals represent like elements, and in which.

DETAILED DESCRIPTION OF THE INVENTION

Figure 1:
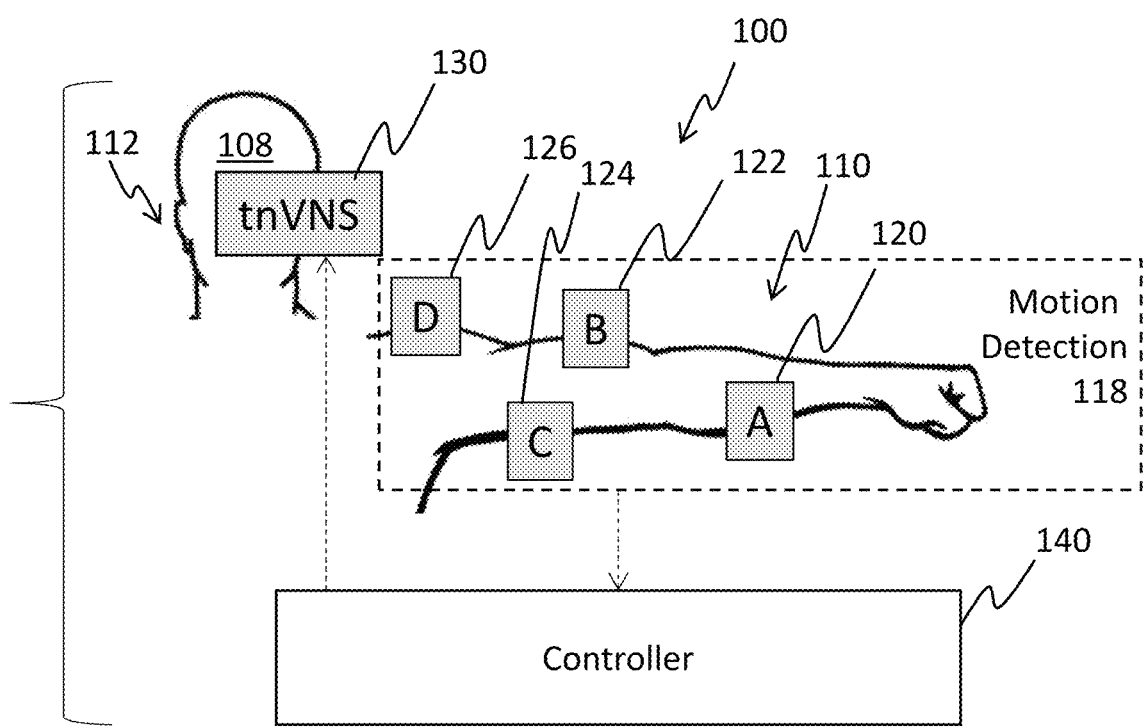
FIG. 1 is a diagram of a neurorehabilitation system according to one embodiment.

It is to be understood that the figures and descriptions of the present invention have been simplified to illustrate elements that are relevant for a more clear comprehension of the present invention, while eliminating, for the purpose of clarity, many other elements found in systems and methods of neurorehabilitation. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Ranges: throughout this disclosure, various aspects of the invention can be presented in a range format. It should be understood that the description in range format is merely for convenience and brevity and should not be construed as an inflexible limitation on the scope of the invention. Where appropriate, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Referring now in detail to the drawings, in which like reference numerals indicate like parts or elements throughout the several views, in various embodiments, presented herein is system and method for neurorehabilitation.

Embodiments of the motor activated auricular vagus nerve stimulation (MAAVNS) described herein utilize a closed-loop system that allows for the simple administration of noninvasive vagus nerve stimulation (VNS) that is precisely paired with motor activity. Because this is closed loop system, the application of this system makes for easy use by rehabilitation therapists in the clinic and can be implemented at at-home, remote or telehealth rehab settings. In one embodiment, vagus nerve stimulation is utilized to enhance motor rehabilitation by increasing neuroplasticity and accelerating the restoration of neural activity and function when paired in a temporally synchronized manner. Embodiments of the system and method described herein implement noninvasive vagus nerve stimulation as an enhancer of neuroplasticity to accelerate motor restoration in post-stroke rehabilitation. In one embodiment, using motion tracking (for example via EMG electrodes, EEG electrodes, infrared cameras, depth cameras, video cameras, pressure mats, accelerometers, real time observers, pneumatics, robotics, or exoskeleton), a computerized system can receive inputs of this movement and deliver simultaneous noninvasive vagus nerve stimulation (electrical stimulation of the auricular branch of the vagus nerve). This movement-induced stimulation allows for intricate pairing of stimulation with movement to enhance the effects of rehabilitation training post-stroke. This neurorehabilitation system can accelerate the time needed for rehabilitation therapy and enhance the magnitude of effects of standard motor therapy of the upper or lower limbs post-stroke. The system can be used for example as a therapeutic tool, a research tool, and/or a tool to enhance rehabilitation of upper and lower limb function post-stroke.

Using motion tracking (e.g. via EMG electrodes, EEG electrodes, infrared cameras, video cameras, pressure mats, accelerometers, real time observers, pneumatics, robotics, or exoskeleton), a computerized system can receive inputs of this movement and deliver simultaneous noninvasive vagus nerve stimulation (electrical stimulation of the auricular branch of the vagus nerve). This movement-induced stimulation allows for intricate pairing of stimulation with movement to enhance the effects of rehabilitation training post-stroke. This neurorehabilitation system can accelerate the time needed for rehabilitation therapy and enhance the magnitude of effects of standard motor therapy of the upper or lower limbs post-stroke. The system can be used for example as a therapeutic tool, a research tool, and/or a tool to enhance rehabilitation of upper and lower limb function post-stroke.

With reference now to FIG. 1, according to one embodiment, a system 100 for neurorehabilitation on a patient 108 includes a motion detector 118 configured to generate a motion detection feedback signal related to motion of the limb 110 being trained. A transcutaneous auricular vagus nerve stimulation module 130 is attached (e.g. via a surface electrode) to the head or neck area 112 of the patient 108 (e.g. the ear). A controller 140 is configured to receive the motion detection feedback signal and send a stimulation signal to the transcutaneous auricular vagus nerve stimulation module 130 based on the motion detection feedback signal meeting a minimum threshold criteria. The transcutaneous auricular vagus nerve stimulation module 130 can include a surface electrode, which in certain embodiments is configured to interface with an anterior wall of an outer ear canal, the tragus or an earlobe. The controller 140 can be connected to motion detection elements wirelessly or by hard wired connections. The controller 140 can be configured to synchronize delivery of the stimulation signal with a detected motion. In one embodiment, the controller 140 delivers the synchronized delivery with a delay of 100 ms or less. In one embodiment, the controller is configured to synchronize delivery of the stimulation signal with a detected motion with a delay of 2 seconds or less. In one embodiment, the controller is configured to synchronize delivery of the stimulation signal with a detected motion with a delay of 1 second or less. In other embodiments, the controller is configured to synchronize delivery of the stimulation signal with the detected motions with a delay of 900 ms, 800 ms, 700 ms, 600 ms, 500 ms, 400 ms, 300 ms, or 200 ms. In other embodiments, the controller is configured to synchronize delivery of the stimulation signal with the detected motions with a delay of 90 ms, 80 ms, 70 ms, 60 ms, 50 ms, 40 ms, 30 ms, 20 ms or 10 ms. The minimum threshold criteria can be a minimum threshold for contraction. In one embodiment, the minimum threshold criteria comprises an EMG motor evoked potential of at least 50 uV. Thresholding EEG may for example require a raw signal to be acquired using EEG electrodes on scalp, signal preprocessed, with feature extraction and classification of a motor movement. In one embodiment, the minimum threshold criteria comprises a motion sufficient to be detectable by an accelerometer. In one embodiment, the minimum threshold criteria comprises a motion sufficient to be detectable via a depth camera, video camera or other visual motion sensor device. In one embodiment, the minimum threshold criteria comprises a force sufficient to trigger a pressure sensing floor mat. In one embodiment, the minimum threshold criteria is determined by an observer and manually triggered.

Motion detection 118 may for example focus on detection motion of various muscle groups, including for example detecting contraction of the forearm (A) 120, biceps (B) 122, Triceps (C) 124 and Anterior/Middle Deltoid (D) 126. Motion detection 118 can be implemented through various modalities such as:

Electromyography (EMG)— Adhesive sensors can be attached to the limb undergoing rehabilitation. Motor evoked potentials will be then measured when motor activity is initiated and can deliver stimulation.

Electroencephalogram (EEG)— Motor activity measured from directly from electrical potentials generated by the brain can be recorded and real-time processed using EEG leads placed over the motor areas of the brain (EEG positions C3, C4) of the patient.

In addition to EMG and EEG, motion detection 118 can be accomplished by a variety of means disclosed herein including, but not limited to accelerometers, infrared or LED tracking cameras, depth or video cameras, pressure mats, or real time observers.

Accelerometers—Wearable sensors can be worn on the wrist or affected limb that is undergoing rehabilitation.

Infrared or LED tracking cameras—Infrared sensors or LED lights can be attached to the limb that is undergoing rehabilitation and camera can track these sensors and lights to determine whether movement occurred.

Depth cameras—Depth cameras (like Xbox Kinect) can track movement without sensors. These can be used to detect movement and initiate stimulation.

Pressure Mats— A pressure mat (like a Q-Pad by Lite-Gait® or other mat commonly employed in rehabilitation environments) can be used to track movement via a pressure sensitive surface. These can be used to detect movement and initiate stimulation.

Real time observers—An individual, other than the patient being stimulated, can observe the patient being stimulated and visually detect movement of the patient and initiate stimulation via a manual trigger.

Thus, in one embodiment, detecting patient motor activity includes utilizing an accelerometer affixed to the patient. In one embodiment, the minimum threshold criteria comprises a force sufficient to trigger a pressure sensing floor mat. In one embodiment, the minimum threshold criteria is determined by an observer and manually triggered. In one embodiment, the muscle activity feedback signals are based on at least one muscle from the group consisting of flexor carpi radialis, flexor capri ulnaris, biceps, triceps, anterior deltoid, middle deltoid, gluteus maximus, quadriceps femoris, anterior compartment of the leg, quadriceps femoris, foot inverters and evertors, biceps femoris, semitendinosus and/or semimembranosus.

The stimulation signal sent by the controller 140 to the transcutaneous auricular vagus nerve stimulation module 130 can in certain embodiments have wherein the stimulation signal has an electrical intensity greater than 0 mA and up to 10 mA, a frequency of greater than 0 Hz and up to 100 Hz, and a pulse width greater than 0µs and up to 500 µs. In one embodiment, the stimulation signal has an electrical intensity greater than 0.5 mA and up to 5 mA, a frequency of greater than 10 Hz and up to 25 Hz, and a pulse width greater than 100 µs and up to 250 µs. In one embodiment, the stimulation signal comprises an electrical intensity greater than 0 mA and up to 10 mA, a frequency of greater than 0 Hz and up to 100 Hz, and a pulse width greater than 0µs and up to 1000 µs. In one embodiment, the stimulation signal comprises an electrical intensity greater than 0.5 mA and up to 5 mA, a frequency of greater than 10 Hz and up to 50 Hz, and a pulse width greater than 100 µs and up to 500 µs. In one embodiment, the stimulation signal comprises an electrical intensity greater than 1 mA and up to 3 mA, a frequency of greater than 25 Hz and up to 50 Hz, and a pulse width greater than 250 µs and up to 500 µs.

In one embodiment, the stimulation is a theta burst stimulation, wherein stimulation is applied in a triplicate pattern in that stimulation is grouped into sets of three burst applied in rapid succession, with an intensity greater than 0 mA and up to 10 mA, more specifically greater than 0.5 mA and up to 5 mA, and most specifically greater than 1 mA and up to 5 mA; wherein each burst within a triplet possesses a frequency greater than 0 Hz and up to 100 Hz, more specifically greater than 25 Hz and up to 75 Hz, and most specifically greater than 40 Hz and up to 60 Hz, and wherein the group of triplets possess a frequency of greater than 0 Hz and up to 100 Hz, more specifically greater than 1 Hz and up to 25 Hz, and most specifically greater than 1 Hz and up to 10 Hz; and a pulse width greater than 0µs and up to 1000 µs, more specifically greater than 100 µs and up to 500 µs, and most specifically greater than 250 µs and up to 500 µs.

In other embodiments the electrical intensity can be 0.1 mA, 0.2 mA, 0.3 mA, 0.4 mA, 0.5 mA, 0.6 mA, 0.7 mA, 0.8 mA, 0.9 mA, 1.0 mA, 1.1 mA, 1.2 mA, 1.3 mA, 1.4 mA, 1.5 mA, 1.6 mA, 1.7 mA, 1.8 mA, 1.9 mA, 2.0 mA, 2.1 mA, 2.2 mA, 2.3 mA, 2.4 mA, 2.5 mA, 2.6 mA, 2.7 mA, 2.8 mA, 2.9 mA, 3.0 mA, 3.1 mA, 3.2 mA, 3.3 mA, 3.4 mA, 3.5 mA, 3.6 mA, 3.7 mA, 3.8 mA, 3.9 mA, 4.0 mA, 4.1 mA, 4.2 mA, 4.3 mA, 4.4 mA, 4.5 mA, 4.6 mA, 4.7 mA, 4.8 mA, 4.9 mA, 5.0 mA, 5.1 mA, 5.2 mA, 5.3 mA, 5.4 mA, 5.5 mA, 5.6 mA, 5.7 mA, 5.8 mA, 5.9 mA, 6.1 mA, 6.2 mA, 6.3 mA, 6.4 mA, 6.5 mA, 6.6 mA, 6.7 mA, 6.8 mA, 6.9 mA, 7.0 mA, 8.1 mA, 8.2 mA, 8.3 mA, 8.4 mA, 8.5 mA, 8.6 mA, 8.7 mA, 8.8 mA, 8.9 mA, 9.0 mA, 9.1 mA, 9.2 mA, 9.3 mA, 9.4 mA, 9.5 mA, 9.6 mA, 9.7 mA, 9.8 mA, 9.9 mA, or 10 mA.

In other embodiments the frequency can be 1 Hz, 2 Hz, 3 Hz, 4 Hz, 5 Hz, 6 Hz, 7 Hz, 8 Hz, 9 Hz, 10 Hz, 11 Hz, 12 Hz, 13 Hz, 14 Hz, 15 Hz, 16 Hz, 17 Hz, 18 Hz, 19 Hz, 20 Hz, 21 Hz, 22 Hz, 23 Hz, 24 Hz, 25 Hz, 26 Hz, 27 Hz, 28 Hz, 29 Hz, 30 Hz, 31 Hz, 32 Hz, 33 Hz, 34 Hz, 35 Hz, 36 Hz, 37 Hz, 38 Hz, 39 Hz, 40 Hz, 41 Hz, 42 Hz, 43 Hz, 44 Hz, 45 Hz, 46 Hz, 47 Hz, 48 Hz, 49 Hz, 50 Hz, 51 Hz, 52 Hz, 53 Hz, 54 Hz, 55 Hz, 56 Hz, 57 Hz, 58 Hz, 59 Hz, 61 Hz, 62 Hz, 63 Hz, 64 Hz, 65 Hz, 66 Hz, 67 Hz, 68 Hz, 69 Hz, 70 Hz, 71 Hz, 72 Hz, 73 Hz, 74 Hz, 75 Hz, 76 Hz, 77 Hz, 78 Hz, 79 Hz, 80 Hz, 81 Hz, 82 Hz, 83 Hz, 84 Hz, 85 Hz, 86 Hz, 87 Hz, 88 Hz, 89 Hz, 90 Hz, 91 Hz, 92 Hz, 93 Hz, 94 Hz, 95 Hz, 96 Hz, 97 Hz, 98 Hz, 99 Hz, or 100 Hz In other embodiments the pulse width can be 10 µs, 20 µs, 30 µs, 40 µs, 50 µs, 60 µs, 70 µs, 80 µs, 90 µs, 100 µs, 110 µs, 120 µs, 130 µs, 140 µs, 150 µs, 160 µs, 170 µs, 180 µs, 190 µs, 200 µs, 210 µs, 220 µs, 230 µs, 240 µs, 250 µs, 260 µs, 270 µs, 280 µs, 290 µs, 300 µs, 310 µs, 320 µs, 330 µs, 340 µs, 350 µs, 360 µs, 370 µs, 380 µs, 390 µs, 400 µs, 410 µs, 420 µs, 430 µs, 440 µs, 450 µs, 460 µs, 470 µs, 480 µs, 490 µs, 500 µs, 510 µs, 520 µs, 530 µs, 540 µs, 550 µs, 560 µs, 570 µs, 580 µs, 590 µs, 610 µs, 620 µs, 630 µs, 640 µs, 650 µs, 660 µs, 670 µs, 680 µs, 690 µs, 700 µs, 710 µs, 720 µs, 730 µs, 740 µs, 750 µs, 760 µs, 770 µs, 780 µs, 790 µs, 800 µs, 810 µs, 820 µs, 830 µs, 840 µs, 850 µs, 860 µs, 870 µs, 880 µs, 890 µs, 900 µs, 910 µs, 920 µs, 930 µs, 940 µs, 950 µs, 960 µs, 970 µs, 980 µs, 990 µs, or 1000 µs.

In certain embodiments, the stimulation signal has a frequency of 15-35 Hz and a pulse width of 150-600 µs, or a frequency of 20-30 Hz and a pulse width of 200-300 µs, or a frequency of 20-30 Hz and a pulse width of 450-550 µs, or a frequency of substantially 25 Hz and a pulse width of substantially 250 µs, or a frequency of substantially 25 Hz and a pulse width of substantially 500 µs. In certain embodiments, the stimulation signal can be theta burst stimulation as further described herein above. Signal waveforms can be for example direct current, alternating current and random noise waveforms.

The signal can also change based on feedback. Physiology monitoring (ie Heart Rate) can indicate whether signal input is working, so physiology may be used to modify the signal intensity to optimize therapy. A reliable biomarker of effective stimulation using taVNS is activation of the parasympathetic nervous system. Various signal intensities may be administered to the user, and physiology monitoring via wearable cardiac sensors can determine whether a reduction in heart rate occurs in response to stimulation. Signal intensity can be varied based on the feedback of this autonomic activation in a closed-loop automated parameter optimization paradigm.

The motion detector 118 can utilize one or more of an EMG electrode, an EEG electrode, a camera, a robotic apparatus, an exoskeleton apparatus, an accelerometer or a real time observer. In one embodiment, the muscle activity feedback signals are based on at least one muscle from the group consisting of flexor carpi radialis, flexor capri ulnaris, biceps, triceps, anterior deltoid, middle deltoid, gluteus maximus, quadriceps femoris, anterior compartment of the leg, quadriceps femoris, foot inverters and evertors, biceps femoris, semitendinosus and/or semimembranosus. In one embodiment, for example, an EMG electrode array can be placed on target muscle groups, including forearm (A) 120, biceps (B) 122, Triceps (C) 124 and Anterior/Middle Deltoid (D) 126. Group muscle movements can be detected at these target locations. The EMG array is used to detect a threshold movement criteria for determining whether a stimulation signal will be delivered. Thus, the motion detection feedback signal can be based on a plurality of muscle activity feedback signals. The muscle activity feedback signals can be based on two or more muscles from the group consisting of flexor carpi radialis, flexor capri ulnaris, biceps, triceps, anterior deltoid and middle deltoid. The Muscle activity signals can be based on at least a first signal from an upper limb indicative of movement from one or more of a trapezius, deltoid, biceps brachii, triceps, flexor/extensor carpi radialis, flexor/extensor digitorum, and flexor/extensor pollicis *brevis*, and at least a second signal from a lower limb indicative of movement from one or more of a gluteus maximus, quadriceps femoris, anterior compartment of the leg, quadriceps femoris, foot inverters and evertors, biceps femoris, semitendinosus and semimembranosus.

Figure 2:
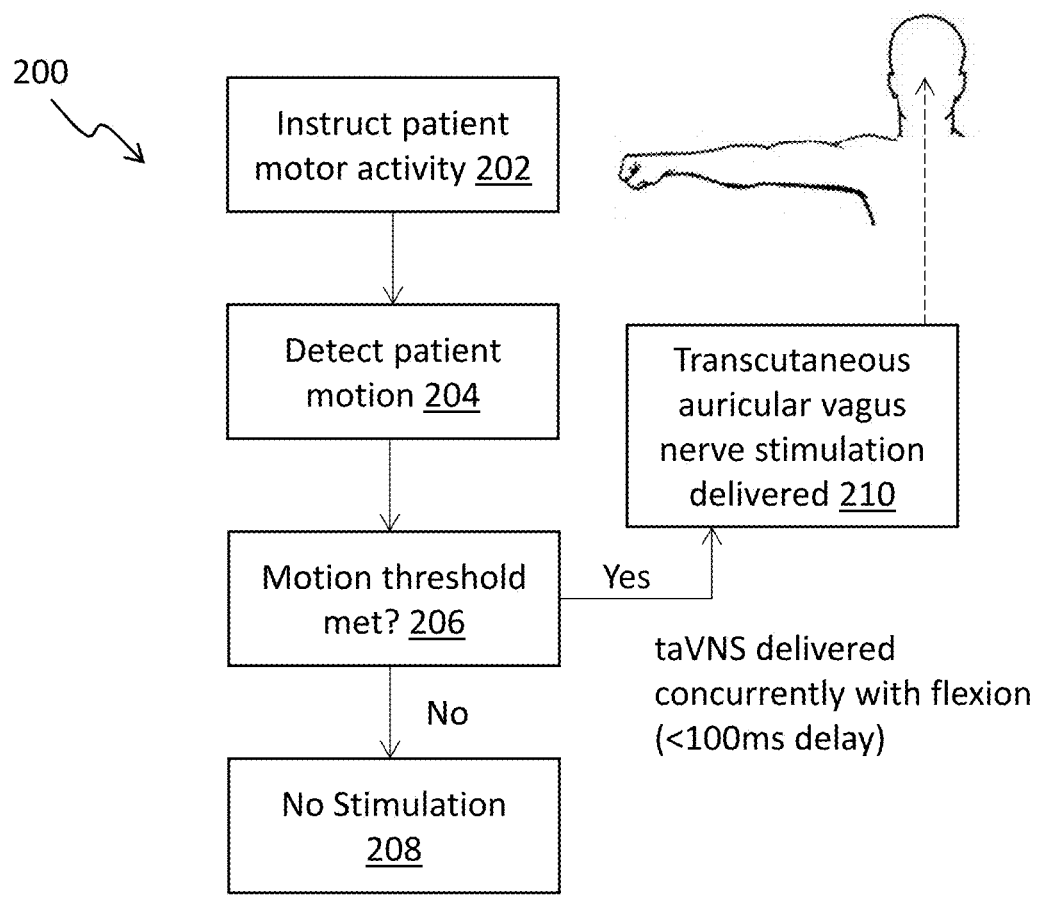
FIG. 2 is a method of neurorehabilitation according to one embodiment.

With reference now to FIG. 2, according to one embodiment, a method 200 for neurorehabilitation includes instructing patient motor activity 202 (e.g. reach, grasp, single joint movement), detecting patient motor activity 204, determining if the detected patient motor activity meets a minimum threshold criteria 206, and stimulating a vagus nerve through transcutaneous auricular vagus nerve stimulation if the minimum threshold criteria is met 210, or otherwise not stimulating if the minimum threshold is not met.

Since the system and method are non-invasive, embodiments of the system and method described herein can also be used for feedback shape and improve any behavioral output, regardless of whether they're recovering from a stroke or otherwise healthy. For example, users could use embodiments of the system and method for skill learning (e.g. developing good golf swing), cognitive tests or motor recovery, or paired with EEG or imaging to correct activation of any part of the brain.

EXPERIMENTAL EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Figure 3:
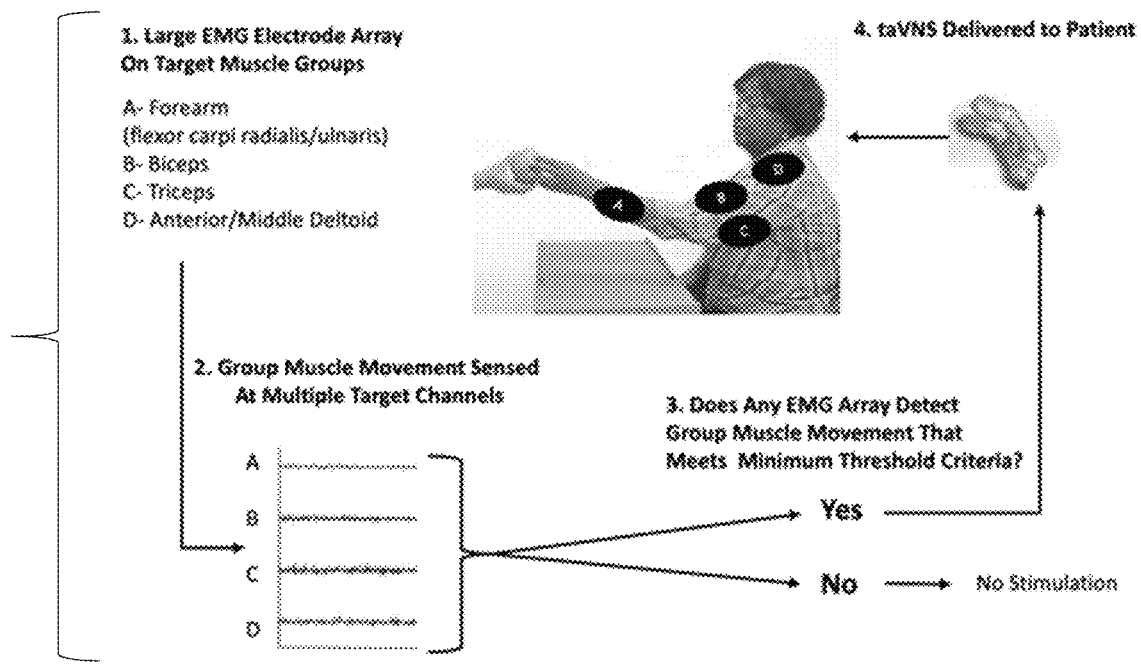
FIG. 3 is an experimental setup showing therapist-guided motor rehabilitation senses motion via EMG electrodes placed on the affected limb of the stroke patient according to one embodiment.

According to one experimental setup, with reference to FIG. 3, according to one embodiment, therapist-guided motor rehabilitation senses motion via EMG electrodes placed on the affected limb of the stroke patient. These EMG electrodes will sense when movement occurs during rehabilitation training, and will deliver noninvasive VNS via ear or neck stimulation electrodes. This system will be setup by the therapist and run independently while the patient receives motor rehabilitation.

Figure 4:
FIG. 4 is an experimental setup showing that robotics utilized as an alternative to standard task-specific motor training administered by a therapist according to one embodiment.

With reference to the experimental setup of FIG. 4, according to one embodiment, robotics and exoskeletons can be utilized as an alternative to standard task-specific motor training administered by a therapist. In this case, a robotic arm can be used in rehabilitation and can send outputs regarding movements making EMG electrodes unnecessary. The robotics can send motion signals to a stimulator which then delivers the noninvasive VNS.

According to one study, system testing was performed in five Patients with unilateral hemiparesis. Five participants (2 female, mean age=62.6) were enrolled with unilateral hemiparesis caused by a stroke (3 ischemic, 2 hemorrhagic). Participants attended a single, 1-hour session where the research team connected the motor activated auricular vagus nerve stimulation (MAAVNS) system to their affected arm.

The MAAVNS system was connected in two different configurations for each participant. MAAVNS hardware was setup identically with the exception of the placement of the electromyography (EMG) sensors-which were placed on either the middle or anterior deltoid.

After connecting the participant to the respective MAAVNS configuration, a therapist instructed them to conducted 3 different movements (reach, pour, and manipulation). Each movement was repeated 8 times. One participants did not complete the manipulation movements due to time constraints. The number of successful MAAVNS trigger in response to upper limb movement was recorded. We also recorded the average time of each movement.

Figure 5A:
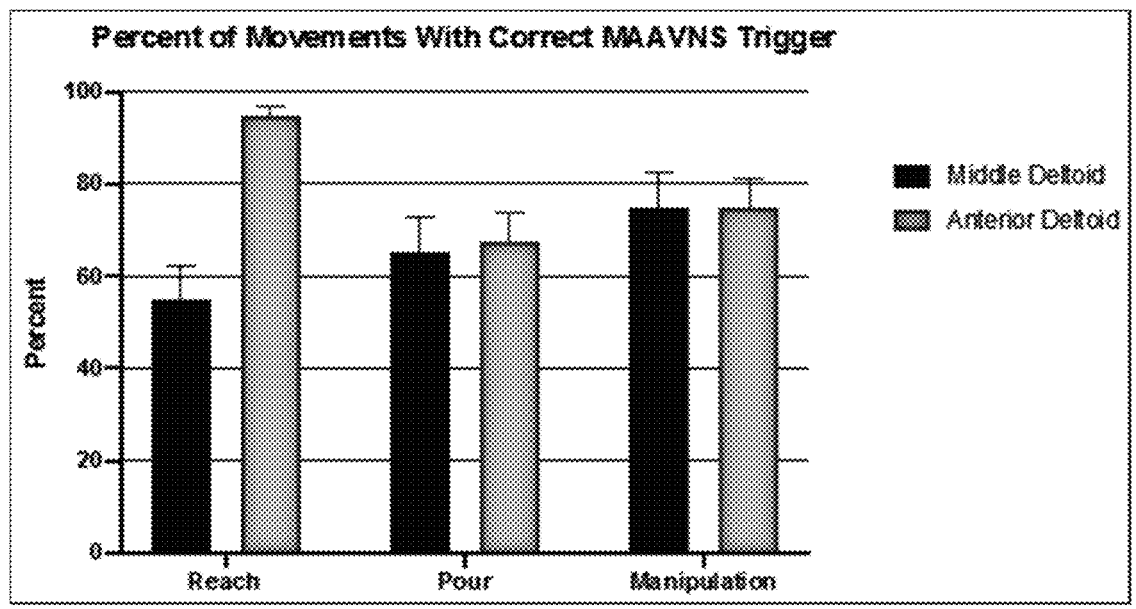
FIG. 5A is a graph of percent of movements with corrects MAAVNS trigger according to one experimental example.

With reference now to the graph in FIG. 5A, the MAAVNS system in the anterior deltoid muscle configuration performed significantly better on reach tasks than middle deltoid (AD: 95% vs MD: 55.1%). Both configurations performed well for alternative movements such as the pour and manipulations.

Figure 5B:
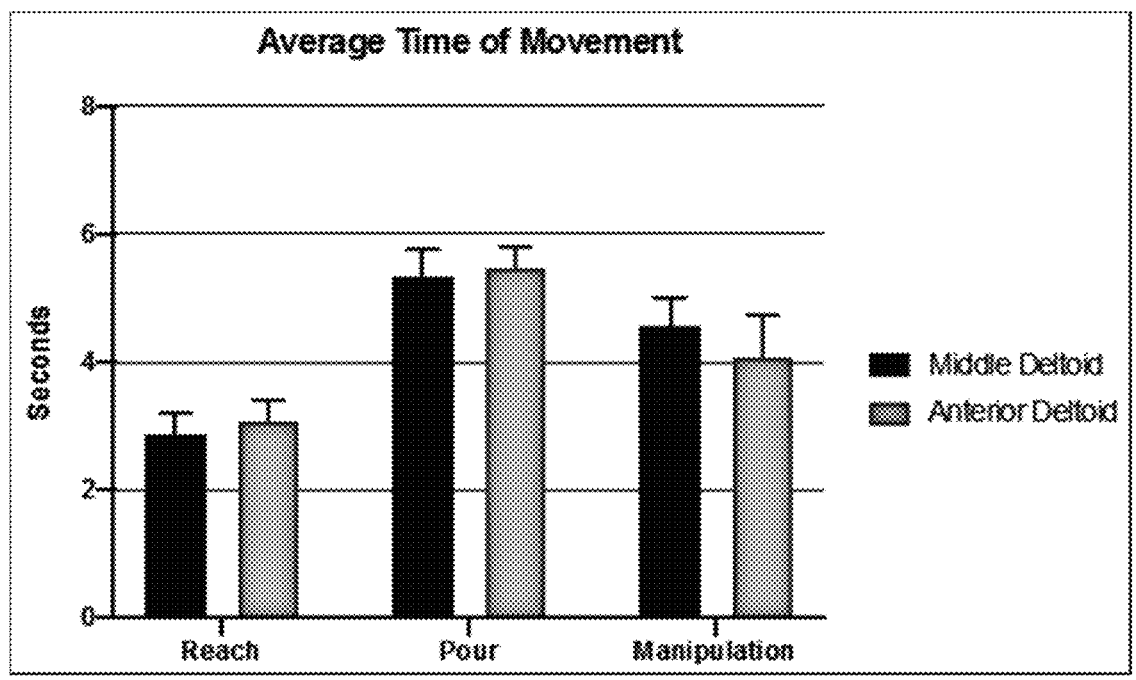
FIG. 5B is a graph of average time of movement according to one experimental example.

With reference now to the graph in FIG. 5B, average timing of movements were consistent between MAAVNS configurations, suggesting the MAAVNS sensors do no impede movements. Furthermore, these data suggest that the amount of stimulation delivered with MAAVNS must be between 2.88 s-5.5 s. This will ensure stimulation is delivered throughout the entire movement.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention.

What is claimed is:

1. A system for neurorehabilitation comprising:
   a motion detector configured to generate a voluntary motion detection feedback signal, the motion detector comprising at least one of an EMG electrode, an EEG electrode, a camera, a robotic apparatus, an exoskeleton apparatus, or an accelerometer;
   a transcutaneous auricular vagus nerve stimulation module; and
   a controller configured to receive the voluntary motion detection feedback signal and send a stimulation signal to the transcutaneous auricular vagus nerve stimulation module with a delay of 2 seconds or less based on the voluntary motion detection feedback signal meeting a minimum threshold criteria for contraction;
   wherein the voluntary motion detection feedback signal is based on a plurality of voluntary muscle activity feedback signals; and
   wherein the muscle activity signals are based on:
      at least a first signal from an upper limb indicative of movement from one or more of a trapezius, deltoid, biceps brachii, triceps, flexor/extensor carpi radialis, flexor/extensor digitorum, and flexor/extensor pollicis *brevis*; and
      at least a second signal from a lower limb indicative of movement from one or more of a gluteus maximus, quadriceps femoris, anterior compartment of the leg, quadriceps femoris, foot inverters and evertors, biceps femoris, semitendinosus and semimembranosus.

2. The system of claim 1, wherein the transcutaneous auricular vagus nerve stimulation module comprises a surface electrode.

3. The system of claim 2, wherein the controller is configured to synchronize delivery of the stimulation signal with a delay of 100 ms or less.

4. The system of claim 3, wherein the stimulation signal comprises an electrical intensity greater than 0 mA and up to 10 mA, a frequency of greater than 0 Hz and up to 100 Hz, and a pulse width greater than 0 μs and up to 500 μs.

5. The system of claim 3, wherein the stimulation signal comprises an electrical intensity greater than 0.5 mA and up to 5 mA, a frequency of greater than 10 Hz and up to 25 Hz, and a pulse width greater than 100 μs and up to 250 μs.

6. The system of claim 1, wherein the minimum threshold criteria comprises an EMG motor evoked potential of at least 50 μV.

7. A method for neurorehabilitation comprising:

detecting voluntary patient motor activity;

determining if the detected voluntary patient motor activity meets a minimum threshold criteria for contraction; and stimulating a vagus nerve with a delay of 2 seconds or less through transcutaneous auricular vagus nerve stimulation if the minimum threshold criteria is met;

wherein the voluntary patient motor activity comprises a plurality of voluntary muscle activity feedback signals including:
- at least a first signal from an upper limb indicative of movement from one or more of a trapezius, deltoid, biceps brachii, triceps, flexor/extensor carpi radialis, flexor/extensor digitorum, and flexor/extensor pollicis *brevis*; and
- at least a second signal from a lower limb indicative of movement from one or more of a gluteus maximus, quadriceps femoris, anterior compartment of the leg, quadriceps femoris, foot inverters and evertors, biceps femoris, semitendinosus and semimembranosus.

\* \* \* \* \*